(12) United States Patent
Miller et al.

(10) Patent No.: US 9,636,905 B2
(45) Date of Patent: May 2, 2017

(54) DEVICE AND METHOD FOR IDENTIFYING A CHANGE IN A PREDETERMINED CONDITION

(71) Applicant: PROTECT ME ALERT SERIES, Mount Royal (CA)

(72) Inventors: Lorne Miller, Montreal (CA); Neil Miller, Montreal (CA)

(73) Assignee: 8372683 Canada, Inc., St-Laurent (CA)

( * ) Notice: Subject to any disclaimer, the term of this patent is extended or adjusted under 35 U.S.C. 154(b) by 97 days.

(21) Appl. No.: 14/444,628

(22) Filed: Jul. 28, 2014

(65) Prior Publication Data
US 2016/0023455 A1    Jan. 28, 2016

(51) Int. Cl.
*B41F 31/00*    (2006.01)
*A61B 5/01*    (2006.01)
(Continued)

(52) U.S. Cl.
CPC ............. *B41F 31/002* (2013.01); *A41D 1/00* (2013.01); *A41D 11/00* (2013.01); *A41D 27/08* (2013.01); *A61B 5/015* (2013.01); *A61B 5/6814* (2013.01); *A63F 2250/1031* (2013.01); *A63H 3/36* (2013.01); *B41F 31/00* (2013.01); *B41M 5/282* (2013.01); *B41M 5/287* (2013.01); *B44F 1/14* (2013.01); *G01D 21/00* (2013.01);
(Continued)

(58) Field of Classification Search
CPC ........ A61B 5/015; A61B 5/6814; G01J 1/419; G01K 1/14; G01K 11/12; A41D 27/08; A41D 1/00; A41D 11/00; B41M 5/287; B41M 5/282; G01D 21/00; B41F 31/00; B41F 31/002; A63H 3/36; B44F 1/14; A63F 2250/1031; Y10S 428/913
USPC ........ 116/200, 201, 206, 207, 216; 2/69, 82, 2/455; 250/472.1
See application file for complete search history.

(56) References Cited

U.S. PATENT DOCUMENTS

| | | | | |
|---|---|---|---|---|
| 2,949,880 A | * | 8/1960 | Fromer | G01J 1/50 250/474.1 |
| 3,903,423 A | * | 9/1975 | Zweig | A61B 5/0059 250/473.1 |

(Continued)

FOREIGN PATENT DOCUMENTS

WO   WO 2010003222 A2 *  1/2010  ........... C09D 131/04

*Primary Examiner* — R. A. Smith
*Assistant Examiner* — Tania Courson
(74) *Attorney, Agent, or Firm* — Cesari and McKenna, LLP

(57) ABSTRACT

In an embodiment, a device and method for identifying a change in a predetermined condition. The device is a patch injected with ink that transforms in response to a change in the predetermined condition, such as, a change in temperature or change in the ultraviolet (UV) index level. The ink includes thermochromic ink that transforms or identifiably changes based on a change in a temperature condition, and/or photochromic ink that transforms or identifiably changes based on a change in an UV index level condition. When temperature increases or decreases to reach one or more threshold temperature values, the thermochromic ink transforms in an identifiable manner to indicate a condition has be met. When the UV index level increase or decrease to reach one or more threshold UV index levels, the photochromic ink transforms in an identifiable manner to indicate that a condition has be met.

20 Claims, 3 Drawing Sheets

(51) Int. Cl.
   *A61B 5/00* (2006.01)
   *G01J 1/42* (2006.01)
   *G01K 11/12* (2006.01)
   *A41D 27/08* (2006.01)
   *B41M 5/28* (2006.01)
   *G01D 21/00* (2006.01)
   *A41D 1/00* (2006.01)
   *A41D 11/00* (2006.01)
   *A63H 3/36* (2006.01)
   *B44F 1/14* (2006.01)

(52) U.S. Cl.
   CPC ............... *G01J 1/429* (2013.01); *G01K 11/12* (2013.01); *Y10S 428/913* (2013.01)

(56) References Cited

U.S. PATENT DOCUMENTS

| | | | | |
|---|---|---|---|---|
| 4,028,118 | A * | 6/1977 | Nakasuji | C08K 5/0041 106/31.19 |
| 4,681,791 | A * | 7/1987 | Shibahashi | B41M 5/287 374/E11.021 |
| 4,725,462 | A * | 2/1988 | Kimura | A63H 3/02 283/97 |
| 4,767,647 | A * | 8/1988 | Bree | B05D 1/30 40/1.5 |
| 5,085,607 | A * | 2/1992 | Shibahashi | A63H 33/22 106/31.16 |
| 5,219,625 | A * | 6/1993 | Matsunami | A63H 3/36 349/199 |
| 5,389,093 | A * | 2/1995 | Howell | A61F 13/42 604/361 |
| 5,503,583 | A * | 4/1996 | Hippely | A63H 33/22 446/14 |
| 6,060,157 | A * | 5/2000 | LaPerre | B44C 1/16 428/212 |
| 6,060,321 | A * | 5/2000 | Hovorka | G01N 31/22 422/421 |
| 6,196,241 | B1 * | 3/2001 | Doolan | A45B 25/18 135/16 |
| 6,228,804 | B1 * | 5/2001 | Nakashima | C09K 9/02 503/201 |
| 6,416,853 | B1 * | 7/2002 | Nakashima | A63H 33/22 428/29 |
| 6,594,927 | B2 * | 7/2003 | Witkowski | G09F 3/0288 40/306 |
| 6,604,854 | B1 * | 8/2003 | Limburg | G01K 11/165 116/207 |
| 6,808,804 | B2 * | 10/2004 | Hotaka | B32B 27/08 428/156 |
| 7,280,441 | B2 * | 10/2007 | MacDonald | A61F 13/42 116/206 |
| 7,370,689 | B2 * | 5/2008 | Wang | A61F 7/03 165/10 |
| 7,458,670 | B2 * | 12/2008 | Kuki | B41J 3/28 347/101 |
| 7,674,747 | B1 * | 3/2010 | Long | D06P 1/004 503/201 |
| 7,738,175 | B2 * | 6/2010 | Steenblik | B44F 1/10 359/619 |
| RE42,628 | E * | 8/2011 | Aperfine | A41D 13/00 2/82 |
| 8,029,190 | B2 * | 10/2011 | MacDonald | A41D 13/00 116/216 |
| 8,827,315 | B2 * | 9/2014 | Waumans | B42D 25/00 235/489 |
| 9,427,048 | B2 * | 8/2016 | James | B29D 35/12 |
| 2004/0158156 | A1 * | 8/2004 | Schneemeyer | A61B 5/01 600/474 |
| 2005/0285050 | A1 * | 12/2005 | Bruce | G01J 1/50 250/474.1 |
| 2008/0289535 | A1 * | 11/2008 | Spector | D06P 1/004 106/31.13 |
| 2010/0012017 | A1 * | 1/2010 | Miller | A61B 5/015 116/201 |
| 2010/0313325 | A1 * | 12/2010 | Ebejer | A41B 13/005 2/80 |
| 2015/0330843 | A1 * | 11/2015 | Bodley | G01K 11/12 116/201 |

* cited by examiner

DEVICE AND METHOD FOR IDENTIFYING A CHANGE IN A PREDETERMINED CONDITION

BACKGROUND OF THE INVENTION

Field of the Invention

The present invention pertains to the field of identification devices and in particular to a device configured to identify a change in a predetermined condition.

Background Information

There are a number of different devices that provide for the evaluation of a condition. For example a thermometer can be used to identify a particular outside temperature or body temperature. This manner in identification can be cumbersome, because, if one thinks there is an elevated body temperature, one must subsequently obtain and utilize a thermometer to determine if there is any concern. Additionally, the current status of other conditions may also be required, for example, sun exposure, moisture level or other conditions. Likewise similar to the use of a thermometer, typically cumbersome identification devices may be required for the evaluation of these other conditions.

SUMMARY OF THE INVENTION

An embodiment of the present invention provides a device and method for identifying a change in a predetermined condition. Illustratively, the device comprises a patch (e.g., made of silicon) and injected with ink. The ink is illustratively configured to transform in response to a change in the predetermined condition, such as, e.g., a change in temperature or a change in the ultraviolet (UV) index level. Illustratively, the ink includes thermochromic ink that transforms or otherwise identifiably changes based on a change in a temperature condition (e.g., cold and heat), and/or photochromic ink that transforms or otherwise identifiably changes based on a change in an UV index level condition. The patch may be attached to an article of clothing, for example, a child's garment. Specifically, when temperature increases or decreases to reach one or more threshold temperature values, the thermochromic ink in the patch transforms in an identifiable manner, such as by changing color, to indicate that a condition has been met (e.g., an environmental condition of "too" hot or "too" cold). Similarly, when the UV index level increases or decreases to reach one or more threshold UV index levels, the photochromic ink in the patch transforms in an identifiable manner, such as by changing color, to indicate that a condition has been met (e.g., an environmental condition of "too" much UV radiation). As such, and based on the condition being met as indicated by the transformation of the ink in the patch, actions can be taken, such as, for example, moving the wearer of the garment that includes the patch out of the environment that caused the condition to be met.

BRIEF DESCRIPTION OF THE DRAWINGS

The invention description below refers to the accompanying drawings, of which.

DETAILED DESCRIPTION OF AN ILLUSTRATIVE EMBODIMENTS

Figure 1A:
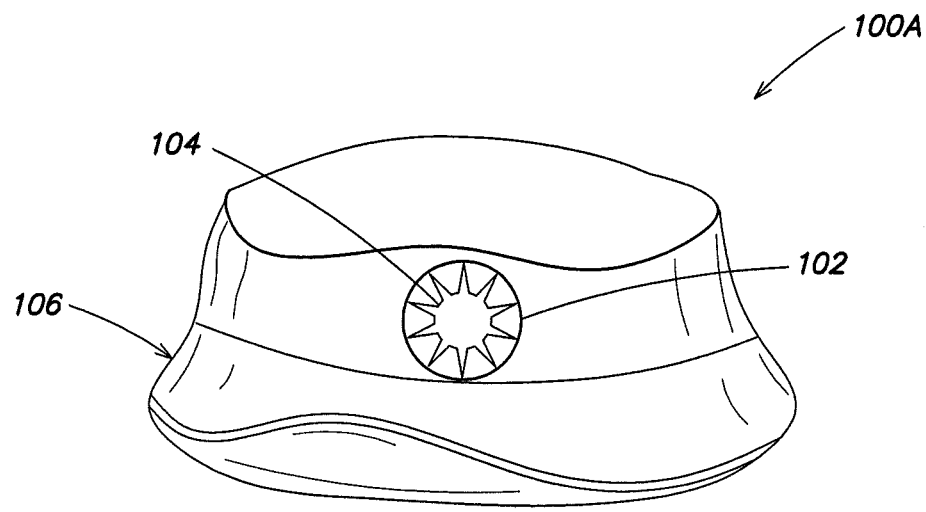
FIG. 1A is an environment that include the patch for identifying a change in a predetermined condition.

FIG. 1A illustrates an environment 100A that includes an exemplary patch 102 injected with thermochromic ink and/or photochromic ink. For example, the thermochromic ink may be a metamorphic ink and the photochromic ink may be Chomazone® ink available from Thermographic Measurements Ltd of Devon, UK. However, it is expressly contemplated that any thermochromic ink and/or photochromic ink may be utilized. Illustratively, the patch 102 is made of silicon and attached to an article of clothing, such as article 106. Patch 102 is shown as a circle, and includes sun 104 that holds or stores the injectable ink. It should be noted that sun 104 is for illustrative purposes. In accordance with alternative embodiments, sun 104 may be depicted in other shapes and/or sizes. As such, the description of sun 104 should be taken as exemplary only. Although the patch is illustratively a circle, patch 102 may be any shape and/or size. More generally, patch 102 may comprise any size and/or shape that may be integrated with a design of article 106. Illustratively, the patch 102 adheres to the article 106 in a known manner. The patch 102 may be adhered to the article 106 or, in alternative embodiments, may be integrated into the article 106. As such, the description of patch 102 being adhered to article 106 should be taken as exemplary only. It should be noted that the description of a hat as an exemplary article 106 is for exemplary purposes and that the principles of the present invention may be utilized with any type of clothing. Illustratively, and as shown in FIG. 1A, the color of the sun 104, that stores the ink, is clear.

Figure 1B:
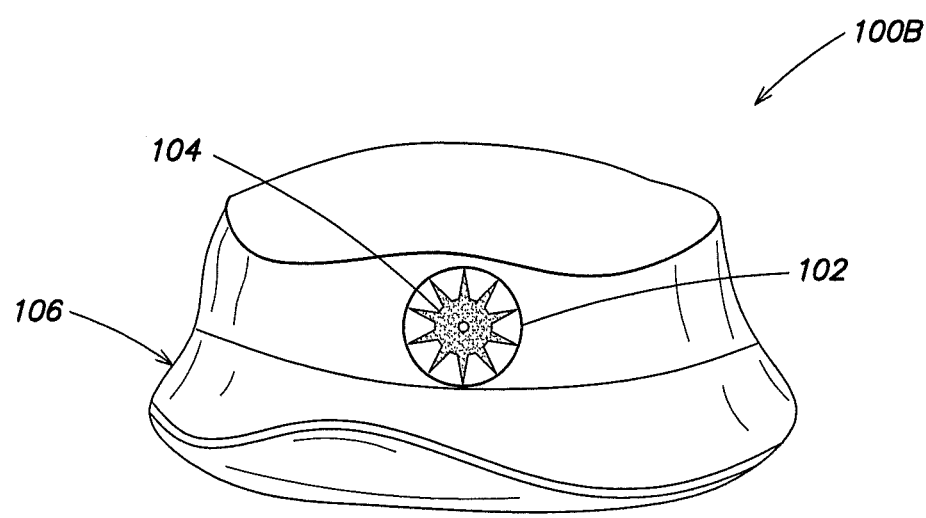
FIG. 1B is an environment that include the patch for identifying a change in a predetermined condition.

When a threshold temperature (e.g., 94 degrees Fahrenheit) is reached, the thermochromic ink in the sun 104 of patch 102 transforms or changes color, for example, as shown in environment 100B of FIG. 1B. Similarly, when a threshold UV index level (e.g., UV index reading of 4) is reached, the photochromic ink in sun 104 of patch 102 transforms or changes color, for example, as shown in environment 100B of FIG. 1B. Illustratively, the threshold temperature and threshold UV index level are associated with the changing of "predetermined conditions" from an existing or initial value, with reference to an entity including but not limited to a living being or inanimate object, to a threshold value or limit. The existing state may also be with reference or regard to the environment proximate to the entity, including but not limited to the atmospheric state proximate to an entity or state of a second entity proximate to a first entity. Examples of existing states, include but are not limited to, temperature state, pressure state, moisture state, UV radiation state, or other state as would be readily understood by a worker skilled in the art.

The identifiable change of the ink can be detected by one or more unassisted human senses or with the assistance of instruments and the like. Illustratively, the identifiable change is a change in color of the inks. Specifically, the thermochromic ink and/or the photochromic ink are configured to visually transform upon a change in the predetermined condition from the initial value to the threshold value, for example the color of the ink can transform in response to changes in temperature, pressure, UV radiation or moisture. The type and reason of occurrence of the transformation of the ink can be directly dependent on the predetermined condition changing form the initial value to the threshold value. For example, ink in the patch can be configured to visually transform upon reaching a particular temperature threshold value or a particular UV index threshold level (e.g., the predetermined condition being met or reached). It is noted that the thermochromic ink and/or photochromic ink are injected into the patch 102 while in a controlled environment. For example, the thermochromic ink and/or photochromic ink are injected into the patch 102 while the injector (e.g., person or machine) is operating in a dark room and the thermochromic ink and/or photochromic ink are not exposed to elevated temperatures and UV radiation.

As shown in environment 100B of FIG. 1B, the ink (e.g., thermochromic ink) in the sun 104 of the patch 102 attached to article 106 may transform or identifiable change from a first color (e.g., a "lighter" color) to a second color (e.g., a "darker" color), when the predetermined condition associated with temperature changes to reach the threshold value (e.g., 94 degrees Fahrenheit in the environment is reached). Similarly, and as shown in environment 100B of FIG. 1B, the ink (e.g., photochromic ink) in the sun 104 of the patch 102 attached to article 106 may transform or identifiably change from a first color (e.g., a lighter color) to a second color (e.g., a darker color), when the predetermined condition associated with UV index levels changes to reach the threshold value (e.g., UV index reading of 4 in the environment is reached).

Figure 1C:
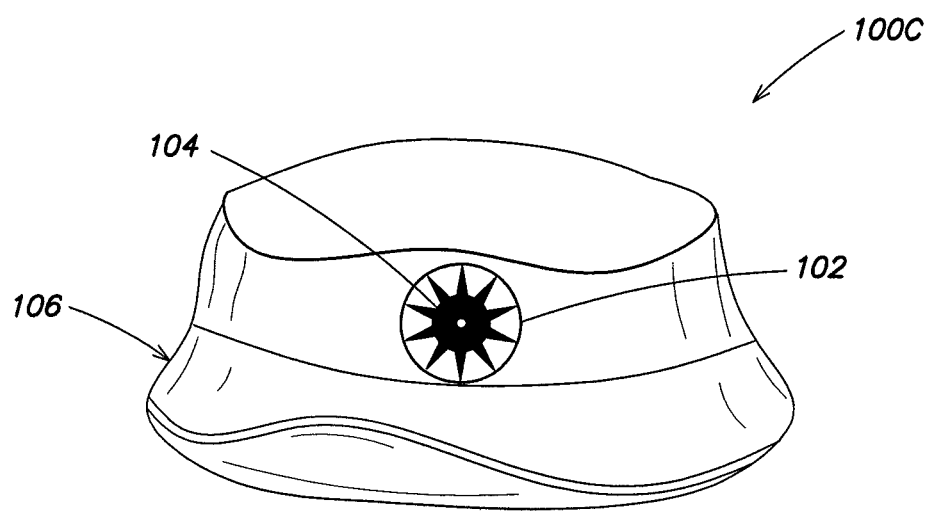
FIG. 1C is an environment that include the patch for identifying a change in a predetermined condition.

FIG. 1C depicts environment 100C that shows the sun 104 of the patch 102 attached to article 106 that has transformed to a third color (e.g., an even darker color than the second color) based on a further threshold being reached. For example, when a further threshold temperature (e.g., 98 degrees Fahrenheit) is reached, the ink (e.g., thermochromic ink) in the sun 104 transforms from the second color (darker color) to a third color (even darker color), as seen in FIG. 1C, to indicate a more "extreme" condition. Similarly, when a further threshold UV level (e.g., UV index reading of 7) is reached, the ink (e.g., photochromic ink) in sun 104 transforms from the second color to a third color (even darker color), as seen in FIG. 1C, to indicate a more extreme condition.

This configuration of the patch 102 provide a means for determining if the wearer of the clothing is being exposed to an undesired level of heat and/or UV radiation. This can enable the prevention of sunburn for example and can provide a means for decreasing the chance of developing skin cancer as it relates to overexposure to sunlight. For example, wearer of the article 106 may be taking out of the sun or environment for a certain period of time. It is noted that when the patch 102 is no longer in the condition where the threshold value has been met, for a predetermined amount of time (e.g., 2 minutes), the ink in the patch 102 will go back to its initial value/first color (e.g., lighter color) as seen in FIG. 1A. This configuration of the patch 102 can be particularly applied to infant or children's clothing, for example T-shirts, shirts or hats. In this manner the patch 102 acts as a visual identifier for a parent can be given a visual identifier, for example the changing of the color of the patch 102 to red, when the infant or child is being exposed to an undesired level of heat and/or ultraviolet radiation.

Figure 2:
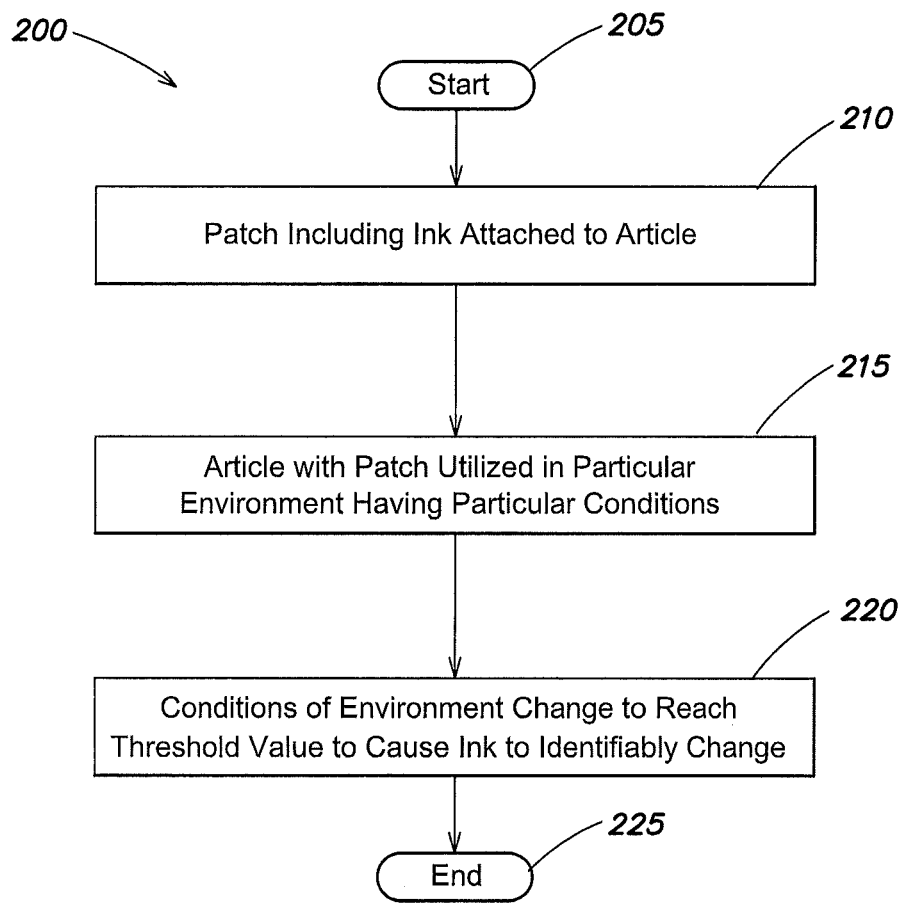
FIG. 2 is a flowchart detailing the steps of a procedure for identifying a change in a predetermined condition in accordance with an illustrative embodiment of the present invention.

FIG. 2 is a flowchart detailing the steps of a procedure for identifying a change in a predetermined condition in accordance with an illustrative embodiment of the present invention. The procedure starts at step 205 and continues to step 210 where a patch 102, injected with thermochromic ink and/or photochromic ink, is placed or attached to an article to be monitored. Specifically, the patch 102 may include a shape, such as sun 104, that stores the ink(s). The article may be an infant's hat, or a cooler intended to store food. At step 215, the article, e.g., infant's hat, with the attached the patch 102 (injected with the thermochromic ink and/or photochromic ink) is utilized in a particular environment having particular conditions. For example, an infant wearing the article 106 with the attached patch 102 may be outside in the sun and exposed to an outside temperature and a particular UV light radiations.

The procedure continues to step 220 where the conditions of the environment change (e.g., change in a predetermined condition) to reach a threshold value causing the ink of patch 102 to transform and identifiably change. Illustratively, the conditions of the environment may cause the thermochromic ink and/or photochromic ink of patch 102 to change visually, and specifically, to change color. Specifically, the thermochromic ink in the patch 102 attached to article 106 transforms or identifiably changes from a first color to a second color, when the conditions of the environment meet or reach a temperature threshold value. More specifically, when temperature increases or decreases to reach one or more threshold temperature values, the thermochromic ink in the patch 102 transforms in an identifiable manner, such as changing color, to indicate that a condition has been met (e.g., an environmental condition of too hot or too cold). For example, a temperature threshold value may be 94 degrees Fahrenheit and initial temperature of the environment may be 88 degrees Fahrenheit. Thus, when the temperature of the environment changes (e.g., change in the predetermined condition) and increases to reach 94 degrees Fahrenheit, the thermochromic ink changes from a first color to a second color, as seen in environment 100B of FIG. 1B.

Similarly, when the UV index level increase or decrease to reach one or more threshold UV index levels, the photochromic ink in the patch 102 transforms in an identifiable manner, such as changing color, to indicate that a condition has been met (e.g., an environmental condition of "too" much UV radiation). For example, a threshold UV index level may be 4 and the initial UV index value may be 2. Thus, when the UV index level of the environment changes and increases to reach the UV index level of 4, the thermochromic ink changes from a first color to a second color, as seen in environment 100B of FIG. 1B.

The procedure continues to step 225, where the procedure ends. It is noted that although the procedure of FIG. 2 describe a single threshold value being reached, it is expressly contemplated that the procedure 200 can utilize one or more additional predetermined conditions. For example, an additional temperature threshold value may be 98 degrees Fahrenheit. Thus, when the conditions of the environment change and reach 98 degrees Fahrenheit, the thermochromic ink changes from a second color to a third color as seen in environment 100C of FIG. 1C.

It is noted that when the patch 102 is no longer in the condition where the change in the predetermined condition has reached the threshold value, for a predetermined amount of time (e.g., 2 minutes), the ink in the patch 102 will go back to the first color (e.g., lighter color), as shown in FIG. 1A. Further, although reference is made to a rise or increase in temperature or UV index level causing the threshold value to be met, a drop or decrease in temperature or UV index level can also cause threshold value to be met. For example, the predetermined condition may be 32 degrees Fahrenheit. As such, when the temperature drops to 32 degrees Fahrenheit, the thermochromic ink changes from the first color to the second color as depicted in FIG. 1B.

The foregoing description has been directed to specific subject matter. It will be apparent, however, that other variations and modifications may be made to the described subject matter, with the attainment of some or all of its advantages. It is expressly contemplated that the procedures, processes, and methods described herein may be implemented in alternative orders. For example, the patch is shaped in order to form a cover for an apparatus, for example a cover for furniture, chairs, stroller, car seats, bags, or other type of cover as would be readily understood by a worker skilled in the art. In alternative embodiments, the patch may be attached to or adhere to, for example a towel, bed sheet, wash cloth, blanket, curtain, bandage, artwork, or other type of sheet-like product as would be readily understood by those skilled in the art. Additionally, the color of the patch is neutral. In another embodiment, the patch is colored. The selection of the color of the patch may be chosen based on the color of the ink being utilized. For example, the color of the patch can be chosen to be the same as that of the ink before it has changed and to contrast with the color of the ink after it has changed in response to stimulus (e.g., temperature UV index level). Moreover, although reference is made to the patch being injected with both thermochromic ink and/or photochromic ink, it is expressly contemplated that the patch could be injected with either thermochromic ink or photochromic ink, individually. Accordingly, this description is to be taken only by way of example and not to otherwise limit the scope of the subject matter described herein. Therefore, it is the object of the appended claims to cover all such variations and modifications as come within the true spirit and scope of the subject matter.

What is claimed is:

1. A device, comprising:
    a silicon patch configured in a particular shape and further configured to be attached to an article, the silicon patch having an area configured to store and hold injectable ink; and
    the injectable ink configured to be injected and stored within the area of the silicon patch, the injectable ink configured to identifiably change based on a change of a predetermined condition from an initial value to a threshold value,
        where the silicon patch visually changes its appearance based on the injectable ink identifiably changing when the predetermined condition changes from the initial value to the threshold value.

2. The device of claim 1, wherein the injectable ink indefinably changes from a first color to a second color when the predetermined condition changes from the initial value to the threshold value.

3. The device of claim 1, wherein the injectable ink includes at least one of thermochromic ink and photochromic ink.

4. The device of claim 1, wherein the injectable ink is configured to identifiably changes in response a changing of a temperature from an initial temperature value to a temperature threshold value.

5. The device of claim 1, wherein the injectable ink is configured to identifiably changes in response to a changing of an ultraviolet (UV) index level value from an initial UV index level value to a threshold UV index level value.

6. The device of claim 1, wherein the injectable ink identifiably changes from a first color to a second color when the injectable ink identifiably changes.

7. The device of claim 6, wherein the injectable ink identifiably changes from the second color to a third color when a further threshold value is reached based on a further change of the predetermined condition.

8. The device of claim 1, wherein the predetermined condition is related to at least one of ultraviolet, temperature level, moisture level, or pressure level.

9. The device of claim 6, wherein the injectable ink identifiably changes from the second color to the first color after a predetermined amount of time and when the threshold value is no longer reached.

10. The device of claim 1, wherein the article is one of an article of clothing, a cooler, and a cover for furniture.

11. A method, comprising:
    providing a patch, attached to an article, the patch injected with at least one type of injectable ink and storing the at least one type of injectable ink, wherein the injectable ink has a first color; and
    transforming of the injectable ink from the first color to a second color based on a change in a predetermined condition from an initial value to a threshold value, wherein the transforming of the injectable ink causes the patch to visually change.

12. The method of claim 11, wherein the injectable ink includes at least one of thermochromic ink and photochromic ink.

13. The method of claim 11, further comprising detecting a change in temperature from an initial temperature value to a threshold temperature value to determine the predetermined condition changed from the initial value to the threshold value, and in response, the injectable ink transforming from the first color to the second color.

14. The method of claim 11, wherein detecting a change in ultraviolet (UV) index level from an initial UV index level value to a threshold UV index level to determine the predetermined condition changed from the initial value to the threshold value, and in response, the injectable ink transforming from the first color to the second color.

15. The method of claim 11, wherein the second color is darker than the first color.

16. The method of claim 11, wherein the injectable ink changes from the second color to a third color when a further threshold value is reached based on a further change of the predetermined condition.

17. The method of claim 16, wherein third color is darker than the second color.

18. The method of claim 11, wherein the predetermined condition is related to at least one of ultraviolet, temperature level, moisture level, or pressure level.

19. The method of claim 11, wherein the injectable ink changes from the second color to the first color after a predetermined amount of time and when the threshold value is no longer reached.

20. The method of claim 11, wherein the change in the predetermined condition is associated with one of an increase in temperature or a decrease in temperature.

* * * * *